US011162066B2

(12) United States Patent
El-Shehawy et al.

(10) Patent No.: US 11,162,066 B2
(45) Date of Patent: Nov. 2, 2021

(54) METHOD FOR DEGRADING MICROCYSTINS IN AN AQUEOUS MEDIUM

(71) Applicant: FUNDACIÓN IMDEA AGUA, Madrid (ES)

(72) Inventors: Rehab El-Shehawy, Alcalá de Henares (ES); María Ángeles Lezcano Vega, Alcalá de Henares (ES); Jesús Morón López, Alcalá de Henares (ES)

(73) Assignee: FUNDACIÓN IMDEA AGUA, Madrid (ES)

( * ) Notice: Subject to any disclaimer, the term of this patent is extended or adjusted under 35 U.S.C. 154(b) by 215 days.

(21) Appl. No.: 16/071,533

(22) PCT Filed: Jan. 20, 2016

(86) PCT No.: PCT/ES2016/070026
§ 371 (c)(1),
(2) Date: Nov. 27, 2019

(87) PCT Pub. No.: WO2017/125619
PCT Pub. Date: Jul. 27, 2017

(65) Prior Publication Data
US 2020/0080161 A1    Mar. 12, 2020

(51) Int. Cl.
*C12N 1/20* (2006.01)
*C12R 1/01* (2006.01)

(52) U.S. Cl.
CPC ............... *C12N 1/205* (2021.05); *C12N 1/20* (2013.01); *C12R 2001/01* (2021.05)

(58) Field of Classification Search
CPC .................................... C12R 1/01; C12N 1/20
See application file for complete search history.

(56) References Cited

PUBLICATIONS

Altschul et al., "Basic Local Alignment Search Tool", Journal of Molecular Biology, 1990, pp. 403-410.
Bohlin et al., "Reliability and Applications of Statistical Methods Based on Oligonucleotide Frequencies in Bacterial and Archaeal Genomes", BMC Genomics, Feb. 2008.
Bouchet et al., "Molecular Genetic Basis of Ribotyping", Clinical Microbiology Reviews, Apr. 2008, pp. 262-273, vol. 21, No. 2.
Chou et al., "Genetic Relatedness Between Listeria monocytogenes Isolates from Seafood and Humans using PFGE and REP-PCR", International Journal of Food Microbiology, Jan. 2006, pp. 135-148.
International Search Report for PCT/ES2016/070026 dated Oct. 14, 2016.
Konstantinidis et al., "Genomic Insights that Advance the Species Definition for Prokaryotes", PNAS, Feb. 2005, pp. 2567-2572, vol. 102, No. 7.
Lahti et al., "Persistence of Cyanobacterial Hepatotoxin, Microcystin-LR in Particulate Material and Dissolved in Lake Water", Water Research, 1997, pp. 1005-1012, vol. 31, No. 5.
Maiden et al., "Multilocus Sequence Typing: A Portable Approach to the Identification of Clones within Populations of Pathogenic Microorganisms", National Academy of Sciences, Mar. 1998, pp. 3140-3145, vol. 95.
Manage et al., "Isolation and Identification of Novel Microcystin-Degrading Bacteria", Applied and Envrionmental Microbiology, Nov. 2009, pp. 6924-6928, vol. 75, No. 21.
Okano et al., "Characteristics of a Microcystin-Degrading Bacterium under Alkaline Environmental Conditions", Journal of Toxicology, 2009.
Park et al., "Degradation of the Cyanobacterial Hepatotoxin Microcystin by a New Bacterium Isolated from a Hypertrophic Lake", Envrionmental Toxicology, 2001, pp. 337-343, vol. 16, No. 4.
Rapala et al., "*Paucibacter toxinivorans* gen. nov., sp. nov., a Bacterium that Degrades Cyclic Cyanobacterial Hepatotoxins Microcystins and Nodularin", International Journal of Systematic and Evolutionary Microbiology, 2005, pp. 1563-1568, vol. 55.
Xiao et al., "Microcystin-LR Biodegradation by *Sphingopyxis* sp. USTB-05", Frontiers of Environmental Science and Engineering, 2011, pp. 526-532.
Zhang et al., "Microbial Biodegradation of Microcystin-RR by *Bacterium sphingopyxis* sp. USTB-05", Journal of Envrionmental Sciences, 2010, pp. 168-175.

*Primary Examiner* — Kade Ariani
(74) *Attorney, Agent, or Firm* — Thompson Coburn LLP; William A. Holtz (57) ABSTRACT

The invention relates to a bacterial strain capable of degrading microcystins in an aqueous medium. A method for reducing the content or for preventing the accumulation of microcystins in an aqueous medium is also disclosed. Finally, the present invention relates to an efficient method for isolating microcystin-degrading microorganisms.

7 Claims, 3 Drawing Sheets

METHOD FOR DEGRADING MICROCYSTINS IN AN AQUEOUS MEDIUM

CROSS-REFERENCE TO RELATED APPLICATIONS

This patent application is 35 U.S.C. § 371 U.S. National Phase Application of International Patent Application No. PCT/ES2016/070026, filed Jan. 20, 2016, which is incorporated by reference herein in its entirety.

FIELD OF THE INVENTION

The invention relates to the field of biological control of microcystins produced by cyanobacterial blooms. In particular, the invention relates to a microorganism from the species *Sphingopyxis* sp. which is able to degrade microcystins in an aqueous medium, to the uses of said microorganism in methods for degrading or preventing the accumulation of microcystins water polluted by cyanobacteria and to a method for isolating microcystin-degrading microorganisms.

BACKGROUND OF THE INVENTION

When closed-water areas such lakes, reservoirs, ponds and inland seas are eutrophicated due to inflow of sewage or the like, a large amount of cyanobacteria, for example, cyanobacteria belonging to the genus *Microcystis*, proliferate to generate the so-called water-bloom. Said cyanobacteria produce microcystins, also known as called toxic water-bloom, and thus the closed-water areas are polluted with microcystins.

Microcystins are cyclic peptides consisting of seven amino acids. Microcystin LR, microcystin RR, and microcystin YR are typical microcystins from closed-water areas. These compounds may poison human or livestock when orally ingested. There are various reports on poisoning by microcystins in several countries.

Conventionally, various methods for treating microcystin polluted water have been reported. In order to prevent poisoning by microcystins, a method for suppressing the generation of water-bloom is generally used. This can be carried out by adding an inhibitor of algae proliferation such as lysine to a closed-water area. In addition, it is also possible to spray an algaecidal copper ion compound over a closed-water area with generated water-bloom. However, said methods of adding an algae proliferation inhibitor causes organic substance pollution, since the algae proliferation inhibitor itself is an organic substance such as lysine. Moreover, algaecidal cause lysis of cyanobacterial cells and release of intracellular microcystins.

Another method for degrading microcystins is based on transmitting ultrasonic waves to polluted water prepared by evacuating a part of a closed-water area with water-bloom generated, thereby crushing cells of water-bloom so as to destroy the algae. However, said method has drawbacks in that oscillation of ultrasonic waves requires a massive amount of energy, and the residual crushed cells cause secondary pollution such as eutrophication. Moreover, the produced microcystins are accumulated in the cells of the cyanobacteria and even if the water-bloom is removed by the above-described method, a large amount of microcystins are released from the crushed cyanobacteria. Therefore, there is a problem that the closed-water area is increasingly polluted with microcystins.

In order to solve this problem, methods based on the microcystin treatment with ozone or with chlorine have been developed. However, in such methods, since ozone or chlorine react with a large amount of contaminants in a closed-water area, there is problem in that microcystins cannot be degraded efficiently. In addition, there is also a problem in that toxic by-products are generated due to the strong oxidation ability of ozone or chlorine.

Thus, an efficient method for degrading microcystins from polluted water is required.

BRIEF DESCRIPTION OF THE INVENTION

In a first aspect, the invention relates to a microorganism from the species *Sphingopyxis* sp. deposited in the Spanish Type Culture Collection (CECT) with accession number CECT 8967 or a mutant thereof which substantially maintains the ability of degrading microcystins.

In a second aspect, the invention relates to a biologically pure culture of the microorganism of the first aspect of the invention.

In a third aspect, the invention relates to a biomass comprising the microorganism of the first aspect of the invention.

In a fourth aspect, the invention relates to a bacterial consortium comprising the microorganism of the first aspect of the invention.

In a fifth aspect, the invention relates to a cell extract of the microorganism of the first aspect of the invention In a sixth aspect, the invention relates to a method for obtaining a biomass of the microorganism of the first aspect of the invention comprising culturing said microorganism under conditions suitable for growth.

In a seventh aspect, the invention relates to a method for preventing the accumulation or for reducing the content of microcystins present in an aqueous medium which comprises adding, to said medium, a microorganism according to the first aspect of the invention or a biologically pure culture according to the second aspect of the invention, a biomass according to the third aspect of the invention, a bacterial consortium according to the fourth aspect of the invention or a cell extract according to the fifth aspect of the invention and maintaining the culture under conditions suitable for the degradation of said microcystins.

In an eight aspect, the invention relates to the use of a microorganism according to the first aspect of the invention, a biologically pure culture according to the second aspect of the invention, a biomass according to the third aspect of the invention, a bacterial consortium according to the fourth aspect of the invention or a cell extract according to the fifth aspect of the invention for preventing the accumulation or for reducing the content of microcystins present in an aqueous medium.

Finally, in a ninth aspect, the invention relates to a method for isolating microcystin-degrading microorganism from an aqueous medium comprising:

i) adding microcystins to a sample obtained from said aqueous medium at an appropriate concentration and incubating the sample under conditions suitable for the growth of microcystin-degrading microorganisms present in the sample, thereby enriching said sample in microcystins degrading microorganisms.

ii) culturing the microorganisms of the sample of step i) on a solid culture medium comprising at least one carbon source and at least one nitrogen source during an appropriate incubation time until colonies are obtained, iii) culturing the microorganism from the colonies obtained of step ii) on a culture medium comprising at least one carbon source and at least one nitrogen source wherein said at least one carbon source and at least one nitrogen source are present in a concentration which is about or lower than the concentration which results after a dilution which is at least a two-fold dilution of the concentration of said components in the culture media of step ii) in the presence of microcystins; and iv) selecting microcystin-degrading microorganisms as the microorganism which grow after the culture step iii).

In another embodiment, the degree of relatedness between the variant and the parent strains is determined as the Tetranucleotide Signature Frequency Correlation Coefficient, which is based on oligonucleotide frequencies (Bohlin J. et al. 2008, BMC Genomics, 9:104). In some embodiments, the Tetranucleotide Signature Frequency Correlation coefficient between the variant and the parent strain is of about 0.99, 0.999, 0.9999, 0.99999, 0.999999, 0.999999 or more but less than 1.

In another embodiment, the degree of relatedness between the variant and the parent strains is determined as the degree of similarity obtained when analysing the genomes of the parent and of the variant strain by Pulsed-field gel electrophoresis (PFGE) using one or more restriction endonucleases. The degree of similarity obtained by PFGE can be measured by the Dice similarity coefficient. In some embodiments, the Dice similarity coefficient between the variant and the parent strain is of about 95%, about, 96%, about 97%, of about 98%, of about 99%, of about 99.1%, of about 99.5%, of about 99.6%, of about 99.7%, of about 99.8%, of about 99.9%, of about 99.99%, of about 99.999%, of about 99.9999%, of about 99.99999%, of about 99.999999% or more but less than 100%.

In another embodiment, a strain is considered a variant of a given parent strain when both strains have the same ribotype, as obtained using any of the methods known in the art an described, for instance, by Bouchet et al. (Clin. Microbiol. Rev., 2008, 21:262-273).

In another embodiment, the degree of relatedness between the variant and the parent strains is the Pearson correlation coefficient obtained by comparing the genetic profiles of both strains obtained by repetitive extragenic palindromic element-based PCR (REP-PCR) (see e.g. Chou and Wang, Int J Food Microbiol. 2006, 110:135-48). In some embodiments, the Pearson correlation coefficient obtained by comparing the REP-PCR profiles of the variant and the parent strain is of about 0.99, 0.999, 0.9999, 0.99999, 0.999999, 0.999999 or more but less than 1.

In another embodiment, the degree of relatedness between the variant and the parent strains is the linkage distance obtained by comparing the genetic profiles of both strains obtained by Multilocus sequence typing (MLST) (see e.g. Maiden, M. C., 1998, Proc. Natl. Acad. Sci. USA 95:3140-3145). In some embodiments, the linkage distance obtained by MLST of the variant and the parent strain is of about 0.99, 0.999, 0.9999, 0.99999, 0.999999, 0.999999 or more but less than 1.

In a preferred embodiment, the variant and the parent strain are of the same genus. In a still more preferred embodiment, the variant and the parent strain are of the same species or subspecies.

The term "microcystins", "MC", or "cyanoginosins", as used herein, refers to a class of toxins produced by certain freshwater cyanobacteria; primarily *Microcystis aeruginosa* but also other *Microcystis* species, as well as members of the *Planktothrix, Anabaena, Anabaenopsis, Oscillatoria* and *Nostoc* genera. Chemically, microcystins are cyclic heptapeptides synthetized nonribosomally by peptide synthases, with a general structure of cyclo-(D-alanine$^1$-X$^2$-D-MeAsp$^3$-Z$^4$-Adda$^5$-D-glutamate$^6$-Mdha$^7$), in which X and Z are variable L-amino acids and Adda refers to a (2S,3S,8S,9S)-3-amino-9-methoxy-2,6,8-trimethyl-10-phenyldeca-4,6-dienoic acid, an unusual amino acid principally responsible of the toxicity of eukaryotic cells. Among 90 MC variants have been characterized but the main isoforms of MC are MC-RR, MC-LR and MC-YR. Variations occur in all amino acids, but most frequently at positions 2 and 4 with variable L-amino acids and at positions 3 and 7 with methylations and demethylations on the D-erythro-methyl-aspartic acid and/or N-methyldehydroalanine. For instance, MC-LR comes from leucine at position 2 and arginine at position 4.

As used herein, the expression "degrading microcystins" refers to the ability of the microorganism of the invention of metabolizing microcystins by using said molecules as a source of carbon and/or nitrogen in presence of additional carbon and/or nitrogen sources. The determination of the ability of metabolizing microcystins by the microorganism of the invention may be carried out by any suitable technique which allows the detection and/or quantification of the microcystins-degradation intermediates, such as the linearized (acyclo-) MC-LR (NH2-Adda-Glu-Mdha-Ala-Leu-MeAsp-Arg-OH), the tetrapeptide (NH2-Adda-Glu-Mdha-Ala-OH) and the Adda moiety among others. Illustrative non-limitative techniques which allow the detection of said metabolites include high performance liquid chromatography (HPLC) or liquid chromatography/mass spectrometry (LC/MS). Alternatively, the determination of MC-degrading capacity may be carried out by analyzing the initial and final concentration of microcystins in a given sample after incubation with the microorganism of the invention by HPLC, LC/MS, enzyme-linked inmunoabsorbent assay (ELISA) and/or protein phosphatase inhibition assay. Therefore, as the person in the art will understand, calculations of the degradation rate (i.e. concentration of microcystins/time unit) not only allows the determination of the ability of the microorganism of the invention to degrade microcystins, but also the efficient removal of the microcystins from an aqueous solution.

The microorganism of the invention also refers to a mutant strain thereof which substantially maintains the capacity of degrading microcystins. As it is used herein, the expression "substantially maintains the capacity of degrading microcystins" of the mutant strain according to the invention means that said microorganism maintains at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99% or at least 100% the ability of degrading microcystins when compared with *Sphingopyxis* sp. strain CECT 8967.

In another aspect, the invention relates to a biologically pure culture, hereinafter "the biologically pure culture of the invention" comprising the microorganism of the invention. As it is used herein, the expression "biologically pure culture" refers to a culture in which the microorganism of the invention can be found in a proportion of 95% or higher, for example 96% or higher, 97% or higher, 98% or higher, 99% or higher, or 100%, compared with other organisms present in the culture. As it is used herein, the term "culture" refers to a population of the microorganisms of the invention. A culture can comprise other elements in addition to the microorganism of the invention, such as the culture medium or any other substance that can be added to the culture medium that is beneficial for growth or maintenance. The term "culture medium" or "medium" is recognized in the art and generally refers to any substance or preparation that is used for the culture of live cells. As it is used in reference to a cell culture, the term "medium" includes the components of the environment surrounding the cells. The medium can be solid medium, liquid medium, gaseous medium, or a mixture of the phases and materials. The growth media include liquid culture media as well as liquid media that do not support cell growth. The medium may also include gelatinous media such as agar, agarose, gelatin and collagen matrices. Exemplary gaseous media include the gas phase to which the cells growing in a Petri dish or another solid or semisolid support are exposed. The term "medium" also refers to a material that must be used in a cell culture, even if it has still not been contacted with the cells. In other words, a liquid rich in nutrients prepared for bacterial culture is a medium. Likewise, a powder mixture which when mixed with water or with another liquid becomes suitable for the cell culture can be called a "powder medium". "Defined medium" refers to the media made up of components having a defined chemical constitution (generally purified). The defined media do not contain biological extracts that are not completely characterized, such as meat broth and yeast extract. "Rich medium" includes media designed to support growth of most or all viable forms of a particular species. Enriched media often include complex biological extracts. Any conventional culture medium suitable for *Sphingopyxis* sp known in the art can be used in the present invention, such as, for example, nutrient broth made up of yeast extract proteose peptone (0.5 g/L), casamino acids (0.5 g/L), glucose (0.5 g/L), starch (0.5 g/L), Na-pyruvate (0.3 g/L), $K_2HPO_4$ (0.3 g/L) and $MgSO4.7H_2O$ (0.05 g/L), pH 7.2 or a culture medium comprising $MgSO_4 \cdot H_2O$ (1.12 mg/L), $KH_2PO_4$ (340 mg/L), $ZnSO_4 \cdot H_2O$ (5 mg/L), $CaCl_2$ (14 mg/L), $Na_2MoO_4 \cdot 2H_2O$ (2.5 mg/L), $Na_2HPO_4 \cdot 7H_2O_2$ (670 mg/L), $FeCl_3$(0.13 mg/L), pH 7.

In a further aspect, the invention relates to a biomass comprising the microorganism of the invention. As it is used herein, the term "biomass" refers to the biological material of living organisms, particularly of the microorganism of the invention.

In another aspect, the invention relates to a bacterial consortium comprising the microorganism of the invention. The term "bacterial consortium", as used herein, refers to a natural association of two or more bacterial populations belonging to different species, which act together as a community, in a complex system where everyone benefits from the activities of others. By way of illustration, the bacterial consortium comprising the microorganism of the invention may also comprise microorganisms of the genera *Sphingopyxis* sp., *Sphingomonas* sp. or *Paucibacter* sp.

In a fifth aspect, the invention relates to a cell extract, hereinafter "the cell extract or the extract of the invention", of a microorganism of the invention. The term "cell extract", as used herein, refers to a cellular homogenate, particularly to a cellular homogenate of the microorganism of the invention, which can be in different grades of cell lysis depending on the treatment of the cells. The lysis of the cells of the microorganism of the invention may be done by any suitable method known in the art, such as heat lysis, lysis in basic medium, lysis in acidic medium, enzymatic lysis using enzymes such as proteases or polysaccharide-degrading enzymes (amylases), lysis by means of ultrasounds, mechanical lysis or lysis by means of osmotic shock. These methods can be carried out in a separate or combined manner, and in the case of combined use, they can be carried out simultaneously or sequentially. The degree of cell rupture can be determined by means of microscopic analysis. As the person skilled in the art will understand, the cell extract of the invention is characterized in that it maintains or substantially maintains the ability of degrading microcystins.

The term "microorganism of the invention" has been previously defined in the context of the first aspect of the invention and equally applies to the second, third, fourth and fifth aspect of the invention.

Method for Obtaining a Biomass

In a further aspect the invention relates to a method for obtaining a biomass of the microorganism of the invention, hereinafter "the first method of the invention", comprising culturing said microorganism under conditions suitable for growth.

The term "microorganism of the invention" has been defined in the first aspect of the invention and equally applies to the first method of the invention.

Conditions suitable for growth of the microorganism of the invention will be those conditions which allow microorganism maintenance and multiplication. In a particular embodiment, said conditions comprise culturing the microorganism of the invention in the presence of a culture medium or substrate containing one or several carbon sources, one or several nitrogen sources and inorganic and organic salts at concentrations suitable for obtaining maximum biomass yields. Said medium or substrate can be solid or liquid. The carbon sources consist of monosaccharides, polysaccharides, cereals or plant extracts. The nitrogen sources comprise plant protein hydrolysates, peptones or free, pure or mixed amino acids. The salts are sulfates or phosphates of elements such as Na, Ca, Mg, Fe, or K. In a particular embodiment, the culture medium or substrate contains between 1 and 5 carbon sources, between 1 and 5 nitrogen sources and between 1 and 10 salts. Suitable culture media which can be used for obtaining a biomass of the microorganism of the invention have been mentioned above in the context of the microorganism of the invention.

In a preferred embodiment, the conditions suitable for growth of the microorganism of the invention comprise culturing the microorganism in the culture medium under constant temperature, pH and aeration conditions. Preferably, the temperature is comprised between 15° C. and 35° C., preferably 27° C. Typically, the pH is comprised between 6.0 and 8.0, preferably 7.0. Normally, aeration is achieved by means of stirring at speeds between 50 and 150 rpm. The time during which the microorganism must be kept under conditions suitable for growth is the time needed for the microorganism to reach a concentration corresponding to a minimum substrate to biomass conversion of 80%. Typically, said time of growth for reaching these yields is between 1 and 120 hours.

Once the microorganism growth step has ended, the obtained biomass can be recovered from the used up substrate by applying one or several unit operations which can comprise centrifugation, decantation, filtration or a combination of several of these operations. Therefore, if desired, the first method of the invention additionally comprises a step for separating the biomass from the substrate by means of one or more steps of centrifugation, decantation or filtration, or a combination thereof.

Method for Treating Microcystin-Polluted Water or for Preventing the Accumulation of Microcystins in Water As mentioned above, microcystins are accumulated in aqueous medium due to the proliferation of cyanobacteria. The microorganism of the invention is useful for treating said polluted water or for preventing the accumulation of microcystins in said media. Thus, in a seventh aspect, the invention relates to a method for preventing the accumulation or for reducing the content of microcystins present in an aqueous medium, hereinafter, "the second method of the invention", which comprises adding to said medium a microorganism according to the first aspect of the invention, a biologically pure culture according to the second aspect of the invention, a biomass according to the third aspect of the invention, a bacterial consortium according to the fourth aspect of the invention or a cell extract according to the fifth aspect of the invention and maintaining the culture under conditions suitable for the degradation of said microcystins.

The term "preventing the accumulation of microcystins present in an aqueous medium", as used herein refers to the maintenance of a concentration of microcystins in the aqueous medium which is considered as tolerable concentration according to the World Health Organization. The term "tolerable concentration", as used herein refers to the amount of microcystins which can be ingested without causing health damage. In a particular embodiment of the first method of the invention, the concentration of microcystins is maintained below 1.5 µg/L, preferably below 1 µg/L.

The term "reducing the content of microcystins present in an aqueous medium" as used herein, include not only the elimination of the almost total of microcystins present in said aqueous medium but also the elimination of at least 50%, at least 60%, at least 70%, at least 75%, at least 80%, at least 85%, at least 90%, at least 95%, at least 96%, at least 97%, at least 98% or at least 99% of the microcystins present in said aqueous medium. The initial concentration of microcystins in an aqueous medium may vary within a range. However, in a particular embodiment, said aqueous medium has microcystins concentration about <1 µg/L to 500 µg/L or even higher. Conventional methods can be used for determining the concentration of microcystins in said aqueous medium. Illustrative examples of said methods are mentioned in the context of the first aspect of the invention.

The term "aqueous medium" as used herein, refers to any liquid phase comprising water. In a particular and preferred embodiment of the invention said aqueous medium refers to inland water such lakes, reservoirs, ponds or streams.

The term "microcystins" have been previously defined in the context of the first aspect of the invention. In a particular embodiment of the second method of the invention, said microcystins are selected from the group consisting of microcystin-RR, microcystin-LR, microcystin-YR and combinations thereof.

Conditions suitable for degradation of microcystins in an aqueous medium according to the second method of the invention include said conditions which allow the development and growth of the microorganism of the invention, the biologically pure culture of the invention, the biomass according to the invention or the bacterial consortium. Said conditions also include those that do not inhibit the microcystin-degrading activity of the cell extract. Such conditions include operation under aerobic conditions; a selection of an appropriate temperature; a selection of an appropriate time of incubation of the microorganism, the biologically pure culture, the biomass, the bacterial consortium or the cell extract of the invention with the aqueous medium to be treated; as well as the addition or the omission of nutrients in order that microorganisms can develop their microcystins-degrading activity.

If necessary, the aqueous medium may be supplemented with a carbon source and/or nitrogen source and/or essential nutrients, in order to facilitate the survival of the microorganism of the invention, the biologically pure culture of the invention, the biomass according to the invention or the bacterial consortium of the invention. By way of illustration, in order to optimize the process of the invention, suitable amounts of micronutrient solution, along with magnesium, cobalt, molybdenum and other essential metals, typically in the micromolar order (µM) may be added. In any case, the choice and amount of nutrients and/or micronutrients to be added to the polluted aqueous medium will depend on the composition of said aqueous medium to be treated and on the microbiological demand in each particular case. The person skilled in the art can take appropriate steps to achieve such suitable conditions.

In a particular embodiment, said conditions suitable for degrading microcystins comprise:
temperature between 15° C. and 35° C.
aerobic conditions
pH between 6 and 8 and/or
incubation time between 1 and 120 hours In a preferred embodiment, said conditions comprise incubating said sample at 27° C., under aerobic conditions and during 24 hours. Said incubation may be carried out in absence of light.

In a particular and preferred embodiment, the second method of the invention comprises a previous step wherein the microorganism, the biomass, the biologically pure culture or the bacterial consortium of the invention has been expanded in a culture medium comprising at least one carbon source and at least one nitrogen source in appropriate conditions for growth. Suitable conditions which can be used for growing the microorganism of the invention have been detailed in the context of the first method of the invention. In a preferred embodiment, said step comprises expanding the microorganism of the invention during 24 hours and at 27° C. in a culture medium which comprises yeast extract proteose peptone (0.5 g/L), casamino acids (0.5 g/L), glucose (0.5 g/L), starch (0.5 g/L), Na-pyruvate (0.3 g/L), $K_2HPO_4$ (0.3 g/L) and $MgSO4.7H_2O$ (0.05 g/L), and at pH 7.2.

In a more particular and preferred embodiment, the second method of the invention comprises a previous step wherein the microorganism, the biomass, the biologically pure culture or the bacterial consortium of the invention has been maintained prior to addition to the aqueous medium containing microcystins under nutrient starvation conditions. The term "nutrient starvation conditions", as used herein, refers to growing cells in nutrient deprivation media. Normally, under said conditions, cells do not duplicate. Said step allows depletion of residual carbon and nitrogen sources in order to achieve the maximum velocity of degradation of microcystins by the microorganism of the invention. Typically, nutrient starvation conditions include supplementing the culture medium with micronutrients but without adding carbon or nitrogen sources. Illustratively, said step comprises culturing the microorganism of the invention in a minimum salt medium (MSM) comprising 112 mg/L $MgSO_4·H_2O$, 5 mg/L $ZnSO_4·H_2O$, 2.5 mg/L $Na_2MoO_4·2H_2O$, 340 mg/L $KH_2PO_4$ 670 mg/L $Na_2HPO_4·7H_2O$, 14 mg/L $CaCl_2$, 0.13 mg/L $FeCl_3$ at pH 7.2. The person skilled in the art may use any method known from the state of the art for determining that cells have reached starvation mode such as any suitable method for detecting cell division.

As the person skilled in the art will understand said step should be carried out during an appropriate time which allows cells reaching starvation period but without dying due to the absence of carbon and nitrogen sources. Preferably, said step is carried out during 8 hours, during 9 hours, during 10 hours, during 11 hours, during 12 hours, during 13 hours, during 14 hours, during 15 hours, during 16 hours, during 17 hours, during 18 hours, during 19 hours or during 20 hours. More preferably, said step is carried out during 12-15 hours.

The microorganism, the biomass, the biologically pure culture, the cell extract or the bacterial consortium according to the invention is characterized in that it can degrade microcystins in presence of additional carbon sources. Thus, in another particular embodiment of the second method of the invention, the concentration of total organic carbon in the aqueous medium is from <1 to 300 mg/L.

In another particular embodiment of the second method of the invention, said aqueous medium comprises microcystins in a concentration from 0.1 to 50000 μg/L.

Method for the Isolation of Microcystin-Degrading Microorganisms

The authors of the present invention have developed an efficient method which allows isolating microcystin-degrading microorganisms from an aqueous medium. Thus, in another aspect, the invention relates to a method for isolating microcystin-degrading microorganism from an aqueous medium, hereinafter "the third method of the invention", comprising:

i) adding a microcystin to a sample obtained from said aqueous medium at an appropriate concentration and incubating the sample under conditions suitable for the growth of microcystin-degrading microorganisms present in the sample, thereby enriching said sample in microcystins degrading microorganisms;

ii) culturing the microorganisms of the sample of step i) on a solid culture medium comprising at least one carbon source and at least one nitrogen source during an appropriate incubation time until colonies are obtained, iii) culturing the microorganism from the colonies obtained of step ii) on a culture medium comprising at least one carbon source and at least one nitrogen source wherein said at least one carbon source and at least one nitrogen source are present in a concentration which is about or lower than the concentration which results after a dilution which is at least a two-fold dilution of the concentration of said components in the culture media of step ii) in the presence of microcystins; and iv) selecting microcystin-degrading microorganisms as the microorganism which grow after the culture step iii)

The term "microorganism", "microcystins" and "aqueous medium" have been previously defined.

According to the third method of the invention, the step i) comprises adding microcystins to a sample obtained from said aqueous medium at an appropriate concentration and incubating the sample under conditions suitable for the growth of microcystin-degrading microorganisms present in the sample. This step allows enriching the microcystins-degrading population over the rest of microorganisms present in the sample. The term "enriched" as used herein, refers to a sample which comprises microcystin-degrading microorganisms in a proportion of more than 50%, more than 60%, more than 70% more than 80%, more than 90%, more than 91%, more than 92%, more than 93%, more than 94%, more than 95%, more than 96%, more than 97% more than 98% or more than 99% with respect to the total of the microorganisms of said sample.

The sample used in step i) can be any sample of water suspected of containing microorganisms with microcystin-degrading capacity, for example a water polluted sample due to a cyanobacteria bloom or a non-polluted freshwater isolated from inland waters such as ponds, lakes, reservoirs or streams. In a particular embodiment, said aqueous sample is freshwater. As it will be understand by the person skilled in the art, special care will be taken in order to ensure the survival of the microorganism population of said sample.

A carbon source comprising microcystins susceptible of being degraded by said microorganism is added to said sample and the resulting medium is incubated under conditions allowing the growth of said microorganism. Illustrative conditions which can be used in this step include operation under aerobic conditions; a selection of an appropriate temperature; a selection of an appropriate time of incubation of the microorganism with the aqueous medium. In a particular embodiment, said conditions comprise:

temperature between 15° C. and 35° C.
aerobic conditions and/or
incubation time between 1 and 20 days In a preferred embodiment, said conditions comprise incubating said sample at 27° C., under aerobic conditions and during 15 days. Said incubation may be carried out in absence of light if desired.

The term "appropriate concentration of microcystins", as used herein refers to a concentration of microcystins which favors growth of microcystins-degrading microorganism. Suitable concentration of microcystins which can be used in this step is from about 0.1 mg/L to 10 mg/L. In a particular embodiment, said concentration of microcystins is 1 mg/L. Any type of microcystins can be used in this step. However it is particularly preferred using an extract comprising microcystins. Said extract can be obtained from cyanobacteria. Illustratively, microcystins extraction can be carried out following methanol extraction method, purified through solid phase extraction method (SPE), dried and finally eluted in sterile Milli-Q water.

According to step ii), the third method of the invention comprises culturing the microorganism of the sample of step i) on a solid culture medium comprising at least one carbon source and at least one nitrogen source during an appropriate incubation time until colonies are obtained. Suitable solid culture media which can be used in step ii) include any rich culture medium known by the person skilled in the art. In a particular embodiment, said solid medium comprises yeast extract proteose peptone (0.5 g/L), casamino acids (0.5 g/L), glucose (0.5 g/L), starch (0.5 g/L), Na-pyruvate (0.3 g/L), $K_2HPO_4$ (0.3 g/L), MgSO4.7$H_2O$ (0.05 g/L) and agar (15 g/L) at pH 7.2. As the person skilled in the art will understand, the incubation comprises a selection of appropriate temperature. Preferably, the temperature is comprised between 15° C. and 35° C., preferably 27° C. Said incubation may be carried out in absence of light, if desired.

The incubation is carried out until colonies are obtained. The term "colony" as used herein, refers to individual organisms of the same species living closely together, usually for mutual benefit and which growth on the surface of or within a solid medium, presumably cultured from a single cell. Typically, the incubation time until colonies are obtained is from 1 to 10 days. In a preferred embodiment the incubation time is 7 days. Colonies are selected and, optionally, purified using standard purification methods such as streak plate method.

The third method of the invention comprises in step iii) culturing the microorganisms from the colonies obtained of step ii) on a culture medium, preferably on a liquid culture medium, comprising at least one carbon source and at least one nitrogen source, wherein said at least one carbon source and at least one nitrogen source are present in a concentration which is about or lower than the concentration which results after a dilution which is at least a two-fold dilution of the concentration of said components in the culture media of step ii) in the presence of microcystins. This step provides an advantage for the isolation of microcystins-degrading microorganisms with highly different metabolism since the diluted media used in this step offers an input of nutrients which enhances growing while still allows metabolically active cells to degrade microcystins. In a particular and preferred embodiment of the invention, this step is carried out on a 96-well plate since it allows to perform high number of MC-degrading assays simultaneously, reducing time and costs of reagents.

The medium used in this step for growing cells is a diluted rich medium. Particularly, the medium used in step iii) which has been at least 2-fold diluted, which means that the concentration of the nitrogen and carbon sources in the medium used in step ii) of the present method is at least double than the concentration of said nitrogen and carbon sources in the medium of step iii). Suitable diluted media which may be used in this step include, but are not limited to, the culture medium of step ii) 3-fold diluted, 4-fold diluted, 5-fold diluted, 6-fold diluted, 7-fold diluted, 8-fold diluted, 9-fold diluted, 10 fold-diluted, 20 fold-diluted or more. In a particular and preferred embodiment of the invention the medium which is used in this step results after a fourth-fold dilution of the medium used in step ii). Any suitable diluent which does not interfere with both growing and microcystins-degrading ability of the microorganisms which are being selected can be used. In a preferred embodiment, the diluent is sterile Milli-Q water.

Said step is carried out in presence of microcystins in order to ensure that the microorganisms which are being selected possess the degrading-microcystins ability. Suitable concentrations that can be used in this step are from about 20 µg/L to 50 mg/L. In a particular and preferred embodiment of the invention the concentration of microcystins in step ii) is 0.5 mg/L.

As the person skilled in the art will understand, step iii) is carried out under conditions suitable for growth of the microorganisms degrading microcystins to be isolated according to the invention and which allows the development of their microcystins-degrading ability. Said conditions comprise culturing the microorganism in the culture medium under constant temperature, pH, and aeration conditions during an appropriate time. Preferably, the temperature is comprised between 15° C. and 35° C., more preferably 27° C. Typically, the pH is comprised between 6.0 and 8.0, preferably 7.0. Normally, aeration is achieved by means of stirring at speeds between 50 and 150 rpm. Preferably, the incubation time of said step is from 1 to 10 days, more preferably 6 days.

Finally, the third method of the invention comprises in step iv) selecting microcystins-degrading microorganisms as the microorganisms which grow after the culture step iii).

Uses of the Invention

The invention also relates to the use of the microorganism of the invention for preventing the accumulation or for reducing the content of microcystins present in an aqueous medium.

The invention also relates to the use of the biologically pure culture of the invention for preventing the accumulation or for reducing the content of microcystins present in an aqueous medium.

The invention also relates to the use of the biomass of the invention for preventing the accumulation or for reducing the content of microcystins present in an aqueous medium.

The invention also relates to the use of the bacterial consortium of the invention for preventing the accumulation or for reducing the content of microcystins present in an aqueous medium.

The invention also relates to the use of the cell extract of the invention for preventing the accumulation or for reducing the content of microcystins present in an aqueous medium.

The terms "microorganism", "biologically pure culture", "biomass", "bacterial consortium", "cell extract", "microcystins", "preventing the accumulation of microcystins present in an aqueous medium", "reducing the content of microcystins present in an aqueous medium", "aqueous medium" and the particulars thereof have been previously defined.

The following examples are provided as merely illustrative and are not to be construed as limiting the scope of the invention.

Example 1: Efficient Removal of MC by *Sphingopyxis* sp. Strain CECT 8967 at Different Total Organic Carbon Concentrations in Water Removal of MCs from water with different organic carbon loads by using isolate *Sphingopyxis* sp. strain CECT 8967:

1. Isolated cells from *Sphingopyxis* sp. strain CECT 8967 were incubated in R2A medium [proteose peptone (0.5 g/L), casamino acids (0.5 g/L), glucose (0.5 g/L), starch (0.5 g/L), Na-pyruvate (0.3 g/L), $K_2HPO_4$ (0.3 g/L), and $MgSO4.7H_2O$ (0.05 g/L) at pH 7.2] at 27° C., in the dark and at 120 rpm for 24 hour with initial absorbance of 0.05 measured at 600 nm.
2. To induce nutrients starvation, cells were collected at 5.000 rpm, washed with MSM (Valeria et al., 2006) and resuspended in MSM medium (112 mg/L $MgSO_4 \cdot H_2O$ 5 mg/L $ZnSO_4 \cdot H_2O$, 2.5 mg/L, $Na_2MoO_4 \cdot 2H_2O$, 340 mg/L $KH_2PO_4$ 670 mg/L $Na_2HPO_4 \cdot 7H_2O$, 14 mg/L $CaCl_2$ and 0.13 mg/L $FeCl_3$ at pH 7.2) at 0.05 measured at 600 nm. Cells were then incubated for 14 hours at the same incubation conditions.
3. Following the starvation period, cells were resuspended in various media (MSM, reservoir's water and 4-fold diluted R2A liquid medium) containing 1 mg/L of MC extract at 0.05 measured at 600 nm ($10^8$ $CFU \cdot mL^{-1}$). See TOC concentration from different mediums at Table 1.
4. Incubation was carried on under previously described conditions for 120 hours.

Samples were collected at different time intervals for MC quantification by using Liquid Chromatography/Mass Spectrometry (LC/MS).

TABLE 1

Total organic carbon (TOC) concentrations in different mediums.

| MSM medium (n = 3) | | Reservoir's water (n = 3) | | ¼ R2A medium (n = 3) | |
| --- | --- | --- | --- | --- | --- |
| Average (mg/L) | S.D. (mg/L) | Average (mg/L) | S.D. (mg/L) | Average (mg/L) | S.D. (mg/L) |
| <1.00 | 0.00 | 3.83 | 0.02 | 258.37 | 0.06 |

The isolated bacteria *Sphingopyxis* sp. strain CECT 8967 was able to degrade efficiently 1 ppm of MC extract containing MC-LR, MC-RR and MC-YR in MSM, reservoir's water and 4-fold diluted R2A liquid medium. This strain removed the 90% of MC between 6 and 9 h of incubation regardless of the media used, while *Sphingosinicella microcystinivorans* Y2 (Park et al., 2001, Environ. Toxicol, 16:337-43) and *Paucibacter toxinivorans* 2C20 (Lathi et al., 1997, Water Res., 31: 1005-1012; Rapala et al., 2005, Int. J. Syst. Evol. Microbiol, 55: 1563-1568) (purchased from Leibniz-Institut DSMZ GmbH, and used here as controls for comparison of degradation rates) needed between, at least, 12 and up to 120 h. These results demonstrate the high capacity of our isolate for MC removal.

The average degradation rate of *Sphingopyxis* sp. strain CECT 8967 was 155.81, 198.92 and 123.13 $\mu g \cdot L^{-1} \cdot h$ in MSM, reservoir's water and 4-fold diluted R2A liquid medium, respectively (Table 2), calculated by averaging the rates at each time interval until the 90% of MC concentration was degraded. The strain Y2 showed an average degradation rate of 79.32, 65.00 and 91.03 $\mu g \cdot L^{-1} \cdot h^{-1}$ in MSM, reservoir's water and 4-fold diluted R2A liquid medium, respectively, whilst 2C20 displayed an average rate of 15.68, 24.61 and 12.68 $\mu g \cdot L^{-1} \cdot h^{-1}$ in the same media. It is important to underline the low efficiency of Y2 and 2C20 strains for MC degradation in reservoir's water, being 3-folds and 8-folds lower than IM-1, respectively.

The obtained data demonstrate the high degradation capacity of *Sphingopyxis* sp. strain CECT 8967 regardless of the concentration of total organic carbon present in the solution.

TABLE 2

Microcystins-degradation capacity by bacteria CECT 8967, Y2 and 2C20

| | Degradation rate ($\mu g \, MC \cdot L^{-1} \cdot h^{-1}$) | | |
|---|---|---|---|
| | MSM | Reservoir's water | R2A ¼ |
| CECT 8967 | 155.81 | 198.92 | 123.13 |
| Y2 | 79.32 | 65.00 | 91.03 |
| 2C20 | 15.68 | 24.61 | 12.68 |

Genetic analysis of the 16S rRNA partial gene of *Sphingopyxis* sp. strain CECT 8967 shows high similarity with MC-degrading strains *Sphingopyxis* sp. C-1 (Okano et al., 2009, J. Toxicol., 954291) and *Sphingopyxis* sp. USTB05 (Zhang et al., 2010, J. Envirom. Sci., 22: 168-175), as well as with non-reported MC-degrading strains *Sphingopyxis* sp. NUG4-1, *Sphingopyxis chilensis* DSR12 and *Sphingomonas* sp. IMER-A1-19, among others). The strain C-1 is a pH-dependent MC degrader, able to remove in three hours 1 mg/L of MC-LR in 0.1 M phosphate buffer (pH=6.72) with 0.5 of initial O.D. at 600 nm. Apparently, this degradation rate of 333.33 $\mu g \cdot L^{-1} \cdot h^{-1}$ is greater than what we report for *Sphingopyxis* sp. strain CECT 8967, however a closer look to the results shows that the former strain was only tested with pure MC-LR and only in buffer; conditions that do not correspond to real life scenarios.

In the same way, strain USTB05 was demonstrated to be able to remove 50.2 mg/L of pure MC-RR in 3 days in a 50 mM potassium phosphate buffer and using intracellular enzyme extract instead of living cells. It is also worth noting that experiments done using that high concentration of MC hugely exceed the limits of reality, where in average common concentrations during a cyanobacterial bloom can be 1-500 $\mu g/L$. Experimental setup with MC concentrations near or slightly higher to what is commonly found during and after a cyanobacterial bloom provide better information for a MC degradation process to overcome a real problem of toxicity. Moreover, cyanobacterial breakdown at the end of the bloom period always causes the release of a mixture of different MC variants. In this sense, experiments performed with pure toxins do not represent the reality for an issue of water-borne toxins and their removal. Accordingly, we tested and we suggest the use of MC-extract rather than pure MC variants when testing strain capacity for MC degradation as a method for MC removal during water treatment.

In the biological treatment for the removal of MC in water, the presence of other organic carbon can slow down or totally impair MC degradation due to inherited different affinity of the biodegraders to carbon sources present in water. The use of *Sphingopyxis* sp. strain CECT 8967 overcomes this situation through its metabolic versatility, since it is able to degrade MC with high efficiency regardless of the different total organic carbon concentrations present in the aqueous water. Moreover, the high potential of *Sphingopyxis* sp. strain CECT 8967 for degrading MC in reservoir's water with a natural MC-extract, and its ability to decrease the MC concentration under the guideline threshold value (WHO, 1998), raises the strain as a promising biological tool to solve global problems with MC toxicity in water.

Example 2: Isolation of MC-Degrading Bacteria Using an Optimized Method

Sampling
1. Surface water samples (1 L) were collected from a local reservoir during a cyanobacterial bloom period with sterile polyethylene bottles. Samples were stored in dark at 4° C. during transport.

Enrichment Assay
2. Duplicate water samples (20 ml) were enriched with 1 mg/L of MC extracted from a cyanobacterial bloom. MC extraction was carried out following methanol extraction method, purified through Solid Phase Extraction method (SPE), dried and finally eluted in sterile Milli-Q water. Samples were then incubated at 27° C. in the dark at 120 rpm for 15 days. Negative controls were prepared in duplicate using autoclaved reservoir's water.
3. MC concentration at 0 and 15 days of incubation was quantified as by LC-MS. Only samples showing degradation activity were selected.

Bacterial Isolation
4. After 15 days of incubation, ten-fold serial dilutions of each sample showing degradation activity were prepared and 100 µL from each dilution were plated on R2A medium (Sigma). Plates were incubated at 27° C. in the dark for 7 days.
5. After 7 days of incubation, colonies with different morphology and color were selected and purified using standard purification method, such as streak plate method.

Biodegradation Assay
6. Each isolated colony and positive controls were transferred into R2A liquid medium and incubated under same incubation conditions till late exponential phase. From each liquid culture 100 µL was washed and resuspended in 4-fold diluted R2A liquid medium containing 1 mg/L of MC extract to get a final O.D of 0.2-0.6 at 600 nm.
7. A sterile 96-well plate was prepared with 150 µL of 4-fold diluted R2A liquid medium with 1 mg/L of MC extract and the previous bacterial solution from point 6 was added. A negative control was included.

8. Plates were covered with a sterile film and incubated at 27° C. in the dark at 120 rpm for 6 days.
9. MC concentration was quantified at time 0 and after 6 days of incubation as previously described in step 3.

Our developed method possesses different essential steps for the isolation of indigenous MC-degrading bacteria with highly different metabolisms. This process comprises: sampling, enrichment, bacterial isolation and biodegradation assay.

Sampling was performed in a waterbody with historical bloom occurrences to increase the success of finding bacteria with the ability of using MC as a carbon and/or nitrogen source. Once in the laboratory, the enrichment step with the addition of a MC crude extract causes a positive selection of MC-degrading bacteria from the large bacterial population inhabiting water samples. After 15 days, degradation activity was analyzed and isolation of potentially MC-degrading bacteria was performed on solid medium according to their morphology. In the biodegradation assay, single bacterial colonies were checked simultaneously in a 96-well plate for MC degrading capacity in a diluted-rich medium (4-fold diluted R2A liquid medium) with MC extract. This step provides an advantage for the isolation of MC-degrading bacteria with highly different metabolism with regard to the methods already described. The diluted-rich medium offers an input of nutrients which enhances bacterial growth while still allowing metabolically active cells to degrade microcystins. The R2A medium was chosen for the isolation method because of its features, which allows growth of bacteria after a stress period.

Most of the studies agree with sampling in places where the MC occurrence is known, but great differences are found for the rest of the steps of the isolation method. Some studies consider the MC enrichment as a non-necessary step. However, it is important for positively selecting the MC-degrading population over the rest of the bacterial populations in the water samples. Moreover, MC enrichment in the own natural water sample allows indigenous bacteria to grow without exposing them to further stress compared to enrichments carried on in artificial media. Performing several enrichment subcultures is widely used as a technique for increasing MC-degrading populations in the sample. However, it causes unnecessarily extension of the incubation periods and higher microcystin consumption, thus increasing the overall cost (especially when pure MC is used).

In the isolation process, some authors prepare plates with diluted-rich media or minimal media containing MC to enhance the isolation of MC-degrading bacteria, but the addition of toxin is not strictly necessary if the previous enrichment step is performed with proper concentration of MC and incubation time. Besides, bacterial transference between liquid and solid mediums causes stress conditions that could lead to limited diversity.

Several strategies have been performed to identify MC-degrading bacteria during the isolation process. Most of these experiments were done on minimal media containing MC, which could avoid the growth of some MC-degrading bacteria if they are not capable of using MC as their sole C or N source. Furthermore, nutrient rich media are also not convenient because they may lead to an extended lag phase periods and providing false negatives. To avoid these problems, diluted-rich mediums (4-fold diluted R2A) add a suitable input of nutrients to enhance bacterial growth without disturbing MC degradation activity and shortening the lag phase period. In general, reported biodegradation assays are limited by the use of large volumes, which increases costs of reagents and time to perform the assay on a large number of potentially MC-degrading isolates. In this sense, simultaneous assays on 96-well plates show a great advantage because it allows the simultaneous testing of higher number of bacteria at the same time, reducing time and costs. In the literature, only one simultaneous assay has been described to check for MC degradation (Manage et al., 2009, Appl. Env. Microbiol., 75:6924-6928). It was performed in BiologMT (a 96-well microplate based on a colorimetric measurement) with MC as a single carbon source in a matrix with minimal medium, which may lead to the consequences explained above. However, in our invention we bring a new approach using diluted-rich medium in 96-well plates, reducing time and costs of the assay and minimizing the risk of losing (false negatives) any potentially MC-degrading bacteria.

In the literature, there is no consensus on the concentration of MC used during the enrichment, isolation or during the biodegradation assay. The concentration used ranges from 0.1 to 50,200 µg/L. Moreover, there is no consensus on the use of purified or crude-extract of MC. The use of MC extract from a toxic cyanobacterial bloom mimic the natural conditions at laboratory scale, as well as reduces costs. Most of the experiments have been performed with pure MC-LR since it is the most common and toxic variant described. However, other isoforms are also found in the environment. Our invention leads to the isolation and identification of bacteria capable of degrading the main MC variants (MC-LR, —RR and —YR), and even other MC that may be present in the water, at low cost.

Figure 1:
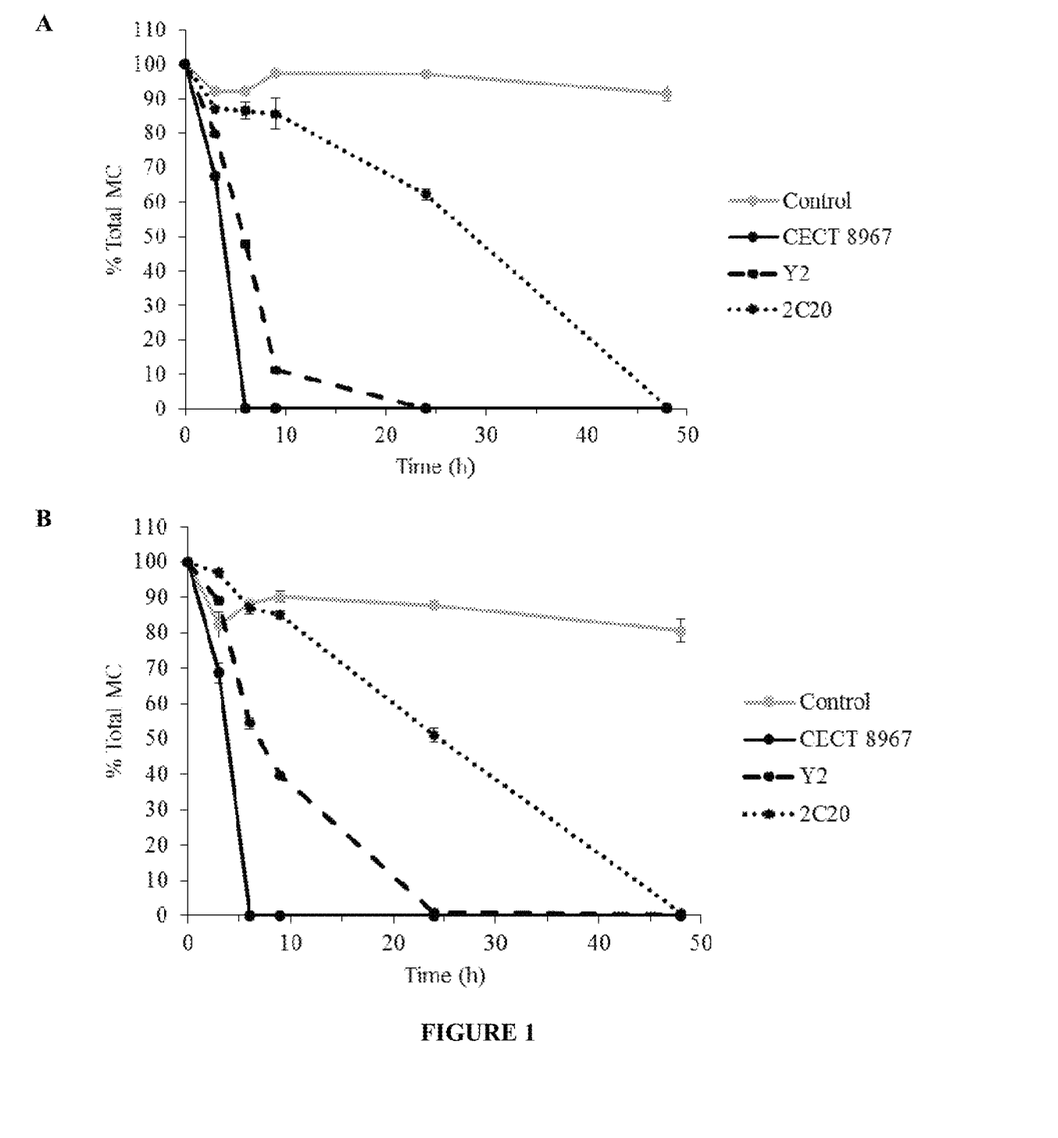
FIG. 1. Total MC degradation by bacteria CECT 8967, Y2 and 2C20 in a) MSM medium, b) reservoir's water and c) 4-fold diluted R2A medium in 48 hours of incubation. Control refers to medium without bacteria. Error bars rel 2592). In some embodiments, the ANI between the variant and the parent strain is of about 95%, about, 96%, about 97%, of about 98%, of about 99%, of about 99.1%, of about 99.5%, of about 99.6%, of about 99.7%, of about 99.8%, of about 99.9%, of about 99.99%, of about 99.999%, of about 99.9999%, of about 99.99999%, of about 99.999999% or more but less than 100%.
Figure 2:
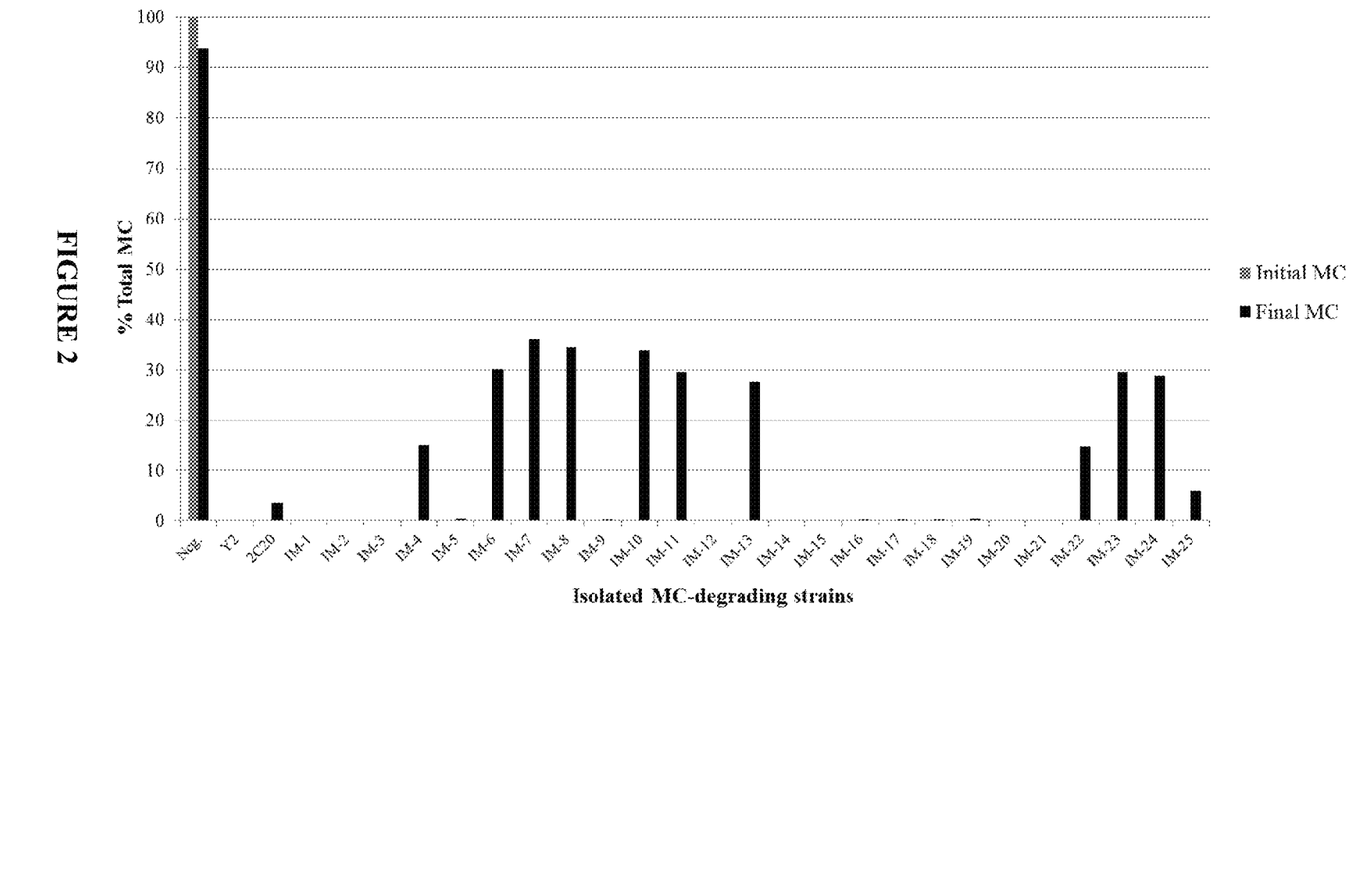

The present invention allows the isolation of a wide range of MC-degrading bacteria with different degradation rates. The low percentage of MC-degrading population from the total bacterial community in the waterbody supposes a challenge for the isolation process. Our described method allowed us to identify 25 strains with different MC degradation ability (FIG. 2) whilst in most of the studies just a single bacterium was reported. Compared with other isolation methods, we achieved to isolate the highest number of degrading bacteria reported with various biodegradation ability that could be used not only as an efficient and environmental-friendly method for MC-removal but also for studying the metabolic pathway(s) of MC degradation allowing us to better understand and sustainably preserve such an important environmental process.

The invention claimed is:

1. A method for preventing the accumulation or for reducing the content of microcystins present in an aqueous medium which comprises adding to said medium a microorganism from the species Sphingopyxis sp. deposited in the Spanish Type Culture Collection (CECT) with accession number CECT 8967 or a mutant thereof which substantially maintains the ability of degrading microcystins, or a biologically pure culture of said microrganism, a biomass comprising said microorganism, a bacterial consortium comprising said microorganism or an extract of said microorganism and maintaining the medium under conditions suitable for the degradation of said microcystins, thereby preventing the accumulation or reducing the content of said microcystins.

2. The method according to claim 1 wherein the microorganism or the biologically pure culture, the biomass, or the bacterial consortium has been expanded in a culture medium comprising at least one carbon source and at least one nitrogen source in appropriate conditions suitable for growth.

3. The method according to claim 1 or 2 wherein the microorganism, the biologically pure culture, the biomass, or the bacterial consortium has been maintained prior to the addition to the aqueous medium containing microcystins under nutrient starvation conditions.

4. The method according to claim 1, wherein the concentration of organic carbon in the aqueous medium is from <1 to 300 mg/L.

5. The method according to claim 1 wherein said aqueous medium comprises microcystins in a concentration from 0.1 µg/L to 50,000 µg/L.

6. The method according to claim 1, wherein said microcystins are selected from the group consisting of microcystin-RR, microcystin-LR, microcystin-YR and combinations thereof.

7. The method according to claim 1, wherein the conditions suitable for degrading microcystins comprise:
- temperature in range between 15° C. and 35° C.
- aerobic conditions
- pH between 6 and 8 and/or
- incubation time between 1 and 120 hours.

* * * * *